US00PP11282P

United States Patent [19]

Yamamoto

[11] Patent Number: Plant 11,282

[45] Date of Patent: Mar. 14, 2000

[54] DENDROBIUM PLANT NAMED 'APOLLON'

[76] Inventor: Jiro Yamamoto, 1-12-30 Hamano, Okayama City, Okayama 700, Japan

[21] Appl. No.: 08/924,664

[22] Filed: Sep. 5, 1997

[51] Int. Cl.[7] ..... A01H 5/00

[52] U.S. Cl. ..... Plt./311

[58] Field of Search ..... Plt./311

[56] References Cited

PUBLICATIONS

Application for Registration of Species (Variety), No. 7027, filed Jul. 21, 1994 (J. Yamamoto, inventor)—copies in English and Japanese.

Certificate of Registration No. 6,425 for Registration Variety Spring Dream Apollon under Japanese Plants Variety Regulation Article 12, Item 4, No. 1, dated May 22, 1998 (copies in English and Japanese).

GTITM UPOVROM Citation for 'Spring Dream Apollo' as per JP PBR 7027, Jul. 21, 1994.

Sander's List of Orchid Hybrids Addendum 1991–1995; pp. 263, 286, 301, 315, 327, 329, 332, and 334.

*Primary Examiner*—Howard J. Locker
*Assistant Examiner*—Kent L. Bell
*Attorney, Agent, or Firm*—Banner & Witcoff, Ltd.

[57] ABSTRACT

A new and distinct variety of orchid, more particularly a Dendrobium hybrid cultivar plant, having durable, pure white flowers is disclosed. The plant's vigorous character and clustered flowers makes it particularly well suited as a small-sized potted plant.

2 Drawing Sheets

DISCOVERY OF THE NEW VARIETY

The orchid of this application was discovered by the applicant in January 1992 as an outstanding member of a large population of seedlings obtained by crossing Dendrobium Seigyoku 'Queen' (unpatented) Dendrobium Cassiope 'Seto' (unpatented). Seigyoku is a cross between Dendrobium Oberon and Dendrobium Spring Wind. Cassiope is a cross between *Dendrobium moniliforme* and *Dendrobium nobile*. These crosses have been registered with The Royal Horticultural Society in England. The mother plant, Seigyoku, is a cross between 'Oberon' and 'Spring Wind' and has large size white flowers, and blooms well. The father plant, Cassiope 'Seto', has white flowers with a soft blurry lavender color at the ouside edges. The center of the flowers is white. These two varieties were cross-bred on Jan. 25, 1989, and their 200 seedlings were cultivated. The first blooms from the seedlings were observed around the middle of January 1992. Among the blooming seedlings were some particularly beautiful white flowers with greenish yellow eyes. The plant of the new variety was immediately recognizable as superior in its flowering and general growth habit to all other seedlings obtained from this cross. Six medium-sized flowers were on each of two canes about 13 cm long. After the new variety had been observed for a period of time its other features of vigorous and early blooming were also noted. Two to three canes were established each year, and more flowers bloomed on each cane. By January 1994, three canes of 20 to 25 cm were established, with a total of 43 flowers.

ASEXUAL REPRODUCTION

Since its discovery in January 1992 the variety has been grown in the applicant's greenhouse at Yamamoto Dendrobium Nursery, Hamano 1-12-30, Okayama City, Japan. During this time a number of plants of the new variety have been asexually reproduced, by the use of stem propagation, tissue culture, and by dividing the plants.

All of the propagations reproduced true to the original in both plant, flower and other characteristics with no signs of mutation. All plants in the variety have continued to be readily distinguishable from both parents in flower quality, plant growth habit and other characteristics. The new variety has been designated as Dendrobium Spring Dream 'Apollon'.

DESCRIPTION OF THE PHOTOGRAPHS

The photographs show the colors of the new variety as nearly true as possible with illustrations of this type.

DESCRIPTION OF THE PLANT AND FLOWERS

Figure 1:
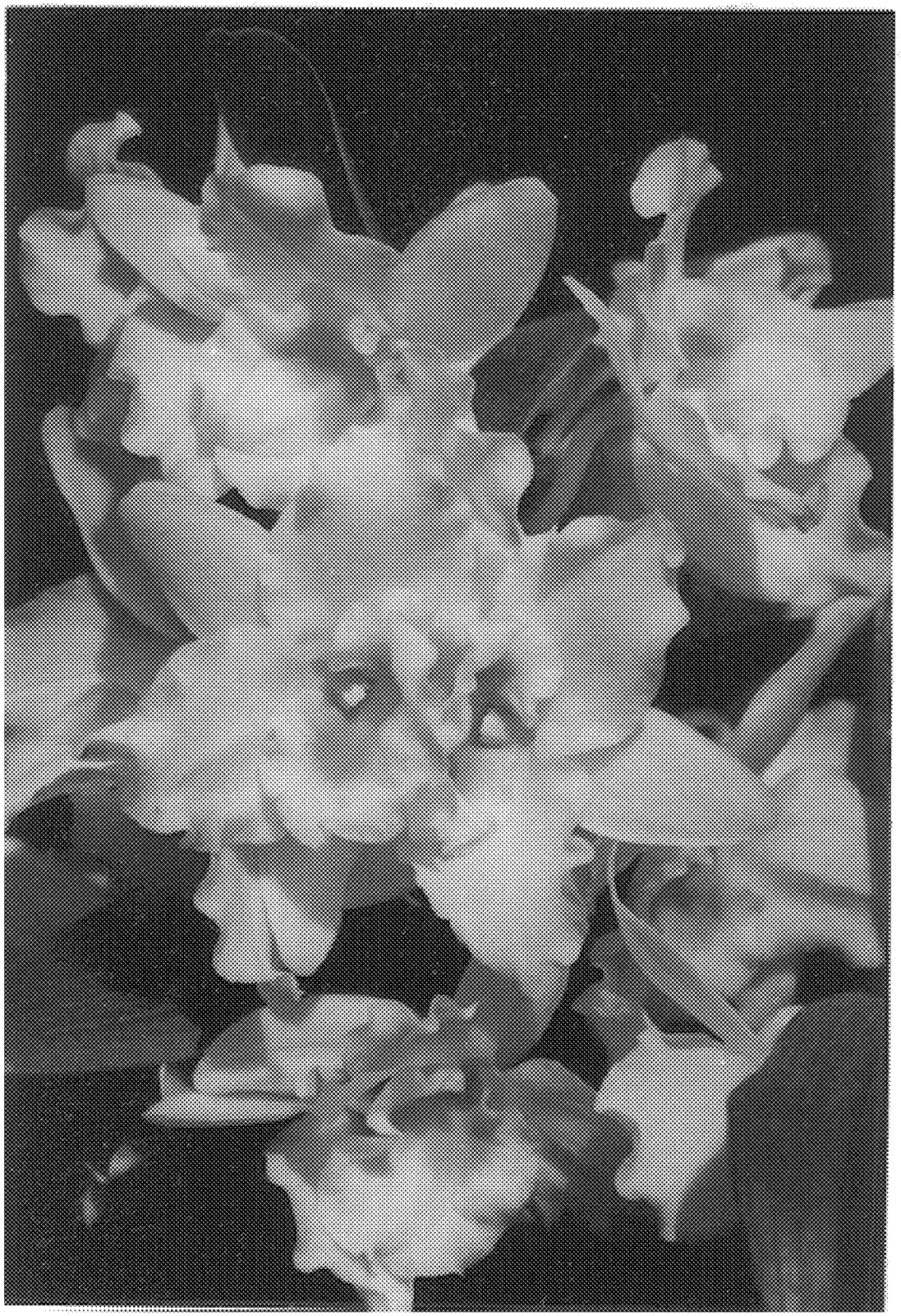
FIG. 1 is a closeup view of a spray of flowers typical of the new variety.
Figure 2:
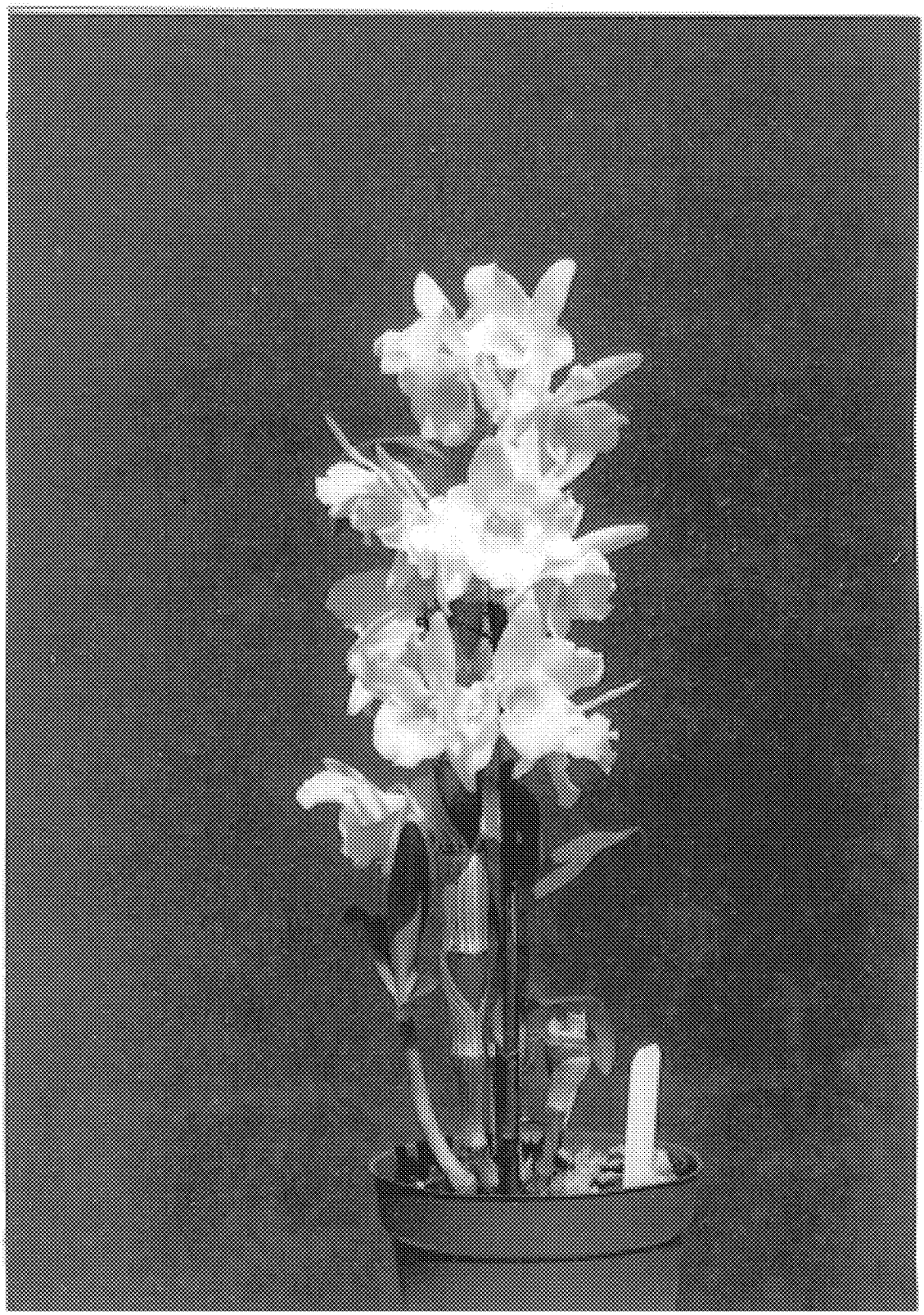
FIG. 2 shows the same flowers but is viewed from a greater distance to reveal the appearance of the flower spray and its relationship to the general size of the plant.

The plant with its flowers is illustrated in the color photographs accompanying this specification. The chart used in the identification of the colors is that of The Royal Horticultural Society (R.H.S Colour Chart). The age of the pseudobulb on the plant described is 1–2 years.

The new variety 'Apollon' is a deciduous orchid and has a number of features which suit it for use as a small-sized potted plant. It has particularly long lasting flowers, which have been observed to bloom continuously for over 20 days. The cane is comparatively sturdy and does not need support most of the time. Two or three canes are established each year, and the canes bloom especially well. By January 1994, three canes of 20 to 25 cm were established, with a total of 43 flowers. The canes have short internodes, and the stems are sturdy. The following internode dimensions are typically observed: top, 2.6 cm long and 1.7 cm wide; bottom, 3.4 cm long and 2.1 cm wide.

The flower is medium sized, about 6 cm in diameter. The plant blooms well, having three flowers on each node. The new variety's flowers are white, with a very slight touch of lavender (78D) at the tip and greenish yellow eyes in the petals and lip. The flowers are of many different shades of white. The plant's short internodes cause the flowers to bloom in clusters. The dorsal and lateral sepals are about 1.3 cm in width, about 3 cm long, and show no waves at the edges. The petals are 2.5 in width, about 3 cm in length, with small waves at the edges.

'Apollon' is a small variety. Compared with the closest comparable variety, Sailor Boy 'Popeye' Dendrobium, the canes of the new variety are shorter, and it grows more vigorously. The flower of 'Popeye' is white with a yellow eye on the lip. 'Apollon', on the other hand, has a white flower with a slight touch of lavender, and a greenish yellow eye in the petals and lip. The plant can be cultivated by standard methods in any area if grown in a greenhouse or vinyl house with a heating system. If the greenhouse is kept at a temperature of over 17° C. at night, new pseudobulbs will appear and will be matured by the middle of July to early August. Within the winter of that same year to the following spring, buds can be seen on the new pseudobulbs. The buds can be small, medium, or large. Small buds (before division into individual buds) are typically 1.4 cm long, 0.5 cm wide, and 145A in color. Medium (individual) buds are typically 1.6 cm long, 0.8 cm wide, and 145B in color. Large (individual) buds are typically 2.6 cm long, 1.3 cm wide, and 145C in color. The shape of the buds is oblong, and their texture is firm. 'Apollon' has the same characteristics as other standard Dendrobium types with respect to cold and heat endurance, as well as flowering period.

The dorsal sepal, lateral sepals, and petals are white in color, with a very slight touch of pink (78D) at the tip, which can fade overtime. There is a slightly greenish yellow eye in the lip. Flower durability is excellent. The plant blooms well even on short canes; on a particular cane which was 13 cm tall, 5 out of 7 nodes bore flowers.

The blooming season is generally four weeks in moderate (75° F.) humid temperatures. At lower temperatures, the plant will bloom over six weeks. When a two-inch cultivated plantlet is replanted, flowers bloom within the year. On the plant, flowers will last at least a month, cut flowers will last about a day.

The stamens, style, and stigmas are fused into a single column, possessing an anther with pollen grains united into a set of two pollinia, which are covered by an anther cap. The stigma is located under the column behind the pollinia. The ovary is inferior, with three carpels present.

Specific features of the plant are listed below.

Size of plant: Small.
Plant posture: Erect.
Pseudobulb:
- *Frontage.*—Narrow rectangular.
- *Cross section.*—Irregular round.
- *Height.*—25–35 mm.
- *Diameter.*—11–20 mm.
- *Color.*—146C.

Leaf
- *General shape.*—Ellipse.
- *Shape of tip.*—Cuspidate; foliage is sessile, with a sheathed base.
- *Vertical cross section.*—Almost flat.
- *Direction of leaf.*—Horizontal.
- *Length.*—12.2 cm.
- *Width.*—4.2 cm.
- *Surface color.*—Green (137B).
- *Underside color.*—Light green (146B).
- *Thickness.*—0.6–1.0 mm.
- *Variegation.*—None.
- *Color of sheath.*—144B.
- *Pubescence on leaf & sheath.*—None.
- *Number of leaves.*—7–10 on largest pseudobulb stem.

Flowers:
- *Arrangement.*—Raceme.
- *Number of blooms per stem.*—3–5.
- *Thickness of flower stem.*—1.1–2.0 mm.
- *Length of flower stem.*—11–30 mm.
- *Color of flower stem.*—157C.
- *Direction of flower stem.*—Slanting upward.
- *Size of bract leaf.*—Wide.
- *Color of bract leaf.*—Light green (144B).
- *Single or double bloom.*—Single.
- *Mode of bloom.*—Holding or flat.
- *Length of spur.*—3–5 mm.
- *Width of flower.*—41–60 mm.
- *Vertical length of flower.*—41–60 mm.
- *Dorsal sepal.*—Shape: elliptical. Tip: Acute. Degree of twist: None. Degree of curl: Flat. Waves at edges: None. Width: 11–15 mm. Length: 21–30 mm. Margin: entire. Base: sessile.
- *Lateral sepals.*—Shape Pointed elliptical. Tip: cuspidate. Degree of twist: None. Direction of curl: Flat. Waves at edges: None. Width: 11–15 mm. Length: 21–30 mm. Margin: entire. Base: sessile, with short mentum, approximately 0.7 to 0.8 cm.
- *Petals.*—Shape: rectangular. Tip: cuspidate. Degree of twist: none. Direction of curl: flat. Waves at edges: slight undulation. Cut at edges: slight. Direction of procusion from stem: perpendicular. Width: 21–30 mm. Length: 31–40 mm. Margin: entire. Base: sessile.
- *Lip shape.*—Oval. Cross section: Flat. Existence of twist: None. Waves at edges: Slight undulation. Cut at edges: Slight. Existence of pubescence: None. Width: 26–30 mm. Length: 21–30 mm. Margin: entire. Base: nearly convolute, open approximately ½–1 times the width of the column.
- *Background color of flower.*—White.
- *Color of dorsal sepal.*—Inner side pattern: Blurred. Inner side base color: 155C. Inner side multicolor area: 78D. Outer side pattern: Blurred. Outer side base color: 155C. Outer side multicolor area: 78D.
- *Color of lateral sepals.*—Inner side base color: 155C. Inner side multicolor area: 78D. Outer side pattern: Blurred. Outer side base color: 155C. Outer side multicolor area: 78D.
- *Petals.*—Inner side pattern: Blurred. Inner side base color: 155C. Inner side multicolor area: 78D. Outer side pattern: Blurred. Outer side base color: 155C. Outer side multicolor area: 75B.
- *Lip.*—Inner side pattern: slightly greenish yellow eye suffusing from the basal portion towards the central portion of the lip. Inner side base color: 155C. Inner side central eye: 150B. Outer side pattern: slightly greenish yellow eye suffusing from the basal portion towards the central portion of the lip. Outer side base color: 155C. Outer side central eye: 145C.
- *Column.*—Outer side pattern: Single color. Outer side base color: 145D.
- *Pollon color.*—155B.
- *Fragrance of flower.*—None.
- *Bloom period.*—Winter/spring.
- *Duration of bloom.*—20 days.
- *Irregularity of flower form.*—None.

*Dropping of lip.*—None.
*Discoloring of lip.*—None.
*Cold and heat durability.*—Temperatures above freezing and up to 104° F.
*Resistance to disease.*—Average; exact durability unknown.
*Resistance to insects.*—Average; exact durability unknown.

*Development of offshoots.*—With too much nitrogen, offshoots emerge from top of cane instead of flowers; otherwise, offshoots emerge from base of plant.

I claim:

1. A new and distinct Orchard plant, as illustrated and described.

* * * * *